(12) United States Patent
Siegel, Jr. et al.

(10) Patent No.: US 6,409,700 B1
(45) Date of Patent: *Jun. 25, 2002

(54) DOUBLE LUMEN CATHETER

(75) Inventors: John M. Siegel, Jr., Huntsville; Vinod B. Makhijani, Madison; Ming Lei, Huntsville; Jagannath Raghavan, Madison, all of AL (US)

(73) Assignee: CFD Research Corporation, Huntsville, AL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/273,571

(22) Filed: Mar. 22, 1999

(51) Int. Cl.$^7$ ................................. A61M 3/00
(52) U.S. Cl. ......................... 604/43; 604/284
(58) Field of Search ................ 604/27–29, 43, 604/264, 284, 508, 522, 523

(56) References Cited

U.S. PATENT DOCUMENTS

| | | | |
|---|---|---|---|
| 4,134,402 A | * | 1/1979 | Mahurkar |
| D272,651 S | | 2/1984 | Mahurkar |
| 4,568,329 A | | 2/1986 | Mahurkar |
| 4,583,968 A | | 4/1986 | Mahurkar |
| 4,692,141 A | | 9/1987 | Mahurkar |
| 4,770,652 A | * | 9/1988 | Mahurkar .................. 604/6.16 |
| 4,808,155 A | | 2/1989 | Mahurkar |
| 4,895,561 A | | 1/1990 | Mahurkar |
| 5,197,951 A | | 3/1993 | Mahurkar |
| 5,221,256 A | | 6/1993 | Mahurkar |
| 5,374,245 A | | 12/1994 | Mahurkar |
| 5,378,230 A | | 1/1995 | Mahurkar |
| 5,486,159 A | | 1/1996 | Mahurkar |
| 5,507,723 A | | 4/1996 | Keshaviah |
| 5,569,182 A | * | 10/1996 | Twardowski et al. |
| 5,571,093 A | * | 11/1996 | Cruz et al. .................. 604/270 |
| 5,685,867 A | | 11/1997 | Twardowski et al. |
| 5,830,196 A | * | 11/1998 | Hicks .......................... 604/523 |
| 5,868,717 A | | 2/1999 | Prosl |

\* cited by examiner

Primary Examiner—Anhtuan T. Nguyen
Assistant Examiner—Michael M Thompson
(74) Attorney, Agent, or Firm—Philip D. Freedman

(57) ABSTRACT

Blood is withdrawn from a vein by a double lumen catheter that has an elongated tube with unitary outer walls. A longitudinal planar septum divides the interior of the tube into an inlet lumen and a longer return lumen. The inlet lumen extends from a proximal end of the tube to an end terminating in a distally forward facing aperture. The return lumen extends contiguously with the inlet lumen from the proximal end of the tube to an end terminating in a distally forward facing aperture spaced in the longitudinal direction distally forward of the inlet lumen aperture. A diverting structure extends from an outer wall of the return lumen distally forward of the aperture of the inlet lumen. The diverting structure diverts flow of treated fluid discharged from the return lumen away from the distally forward facing aperture of the inlet lumen. The blood withdrawn via the catheter is circulated for treatment in a blood purification system.

25 Claims, 2 Drawing Sheets

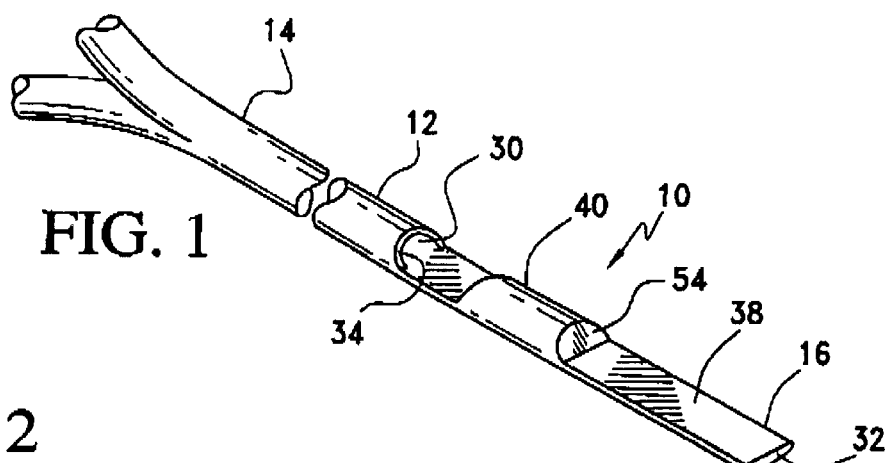
FIG. 1
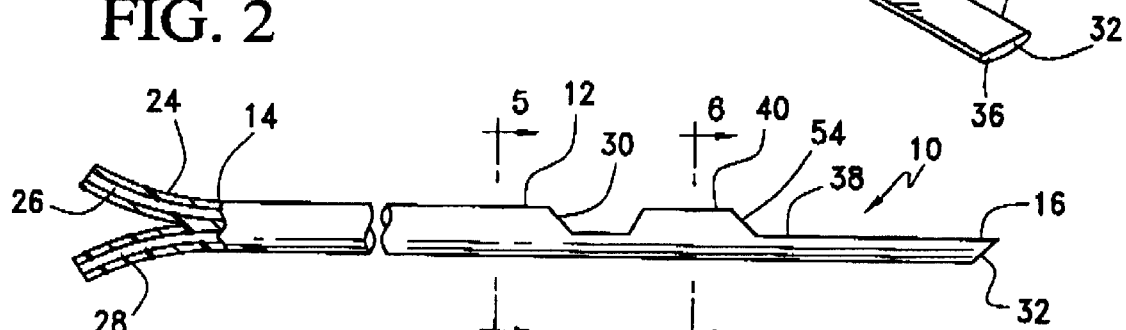
FIG. 3
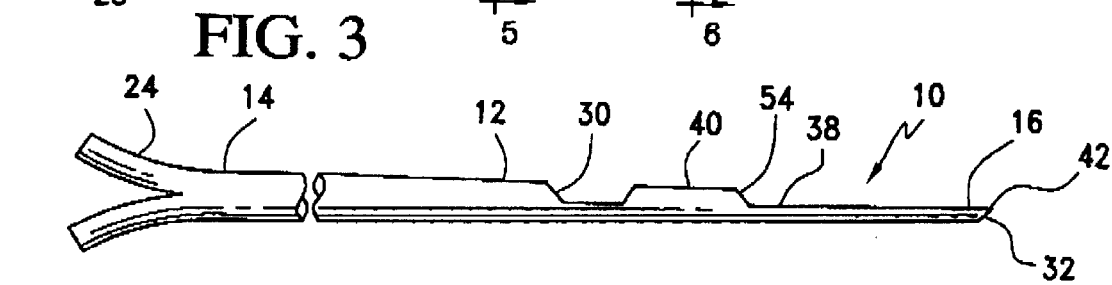
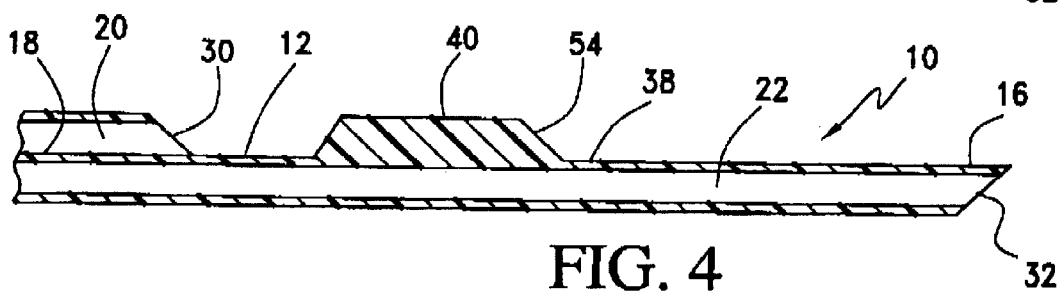
FIG. 4
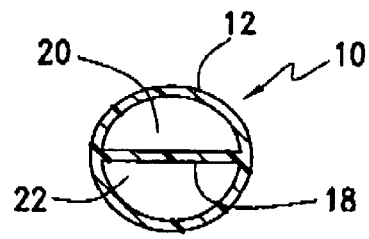
FIG. 5
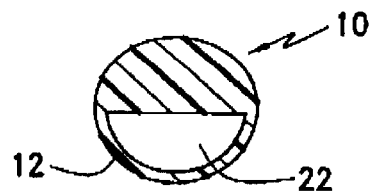
FIG. 6

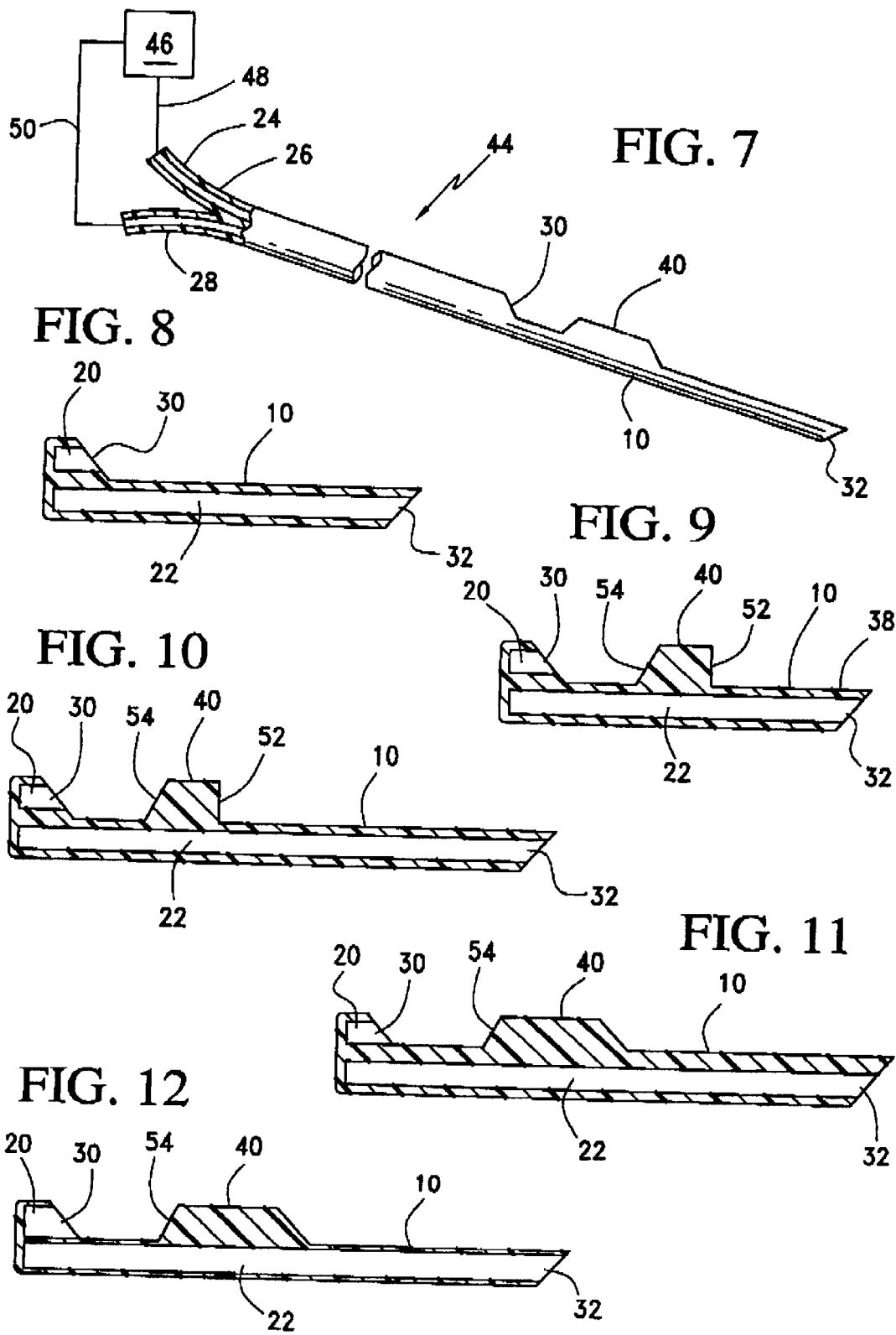

DOUBLE LUMEN CATHETER

BACKGROUND OF THE INVENTION

The present invention relates to a double lumen continuous flow hemodialysis catheter.

Dialysis is a filtration process to separate crystalloid from colloid substances (or smaller molecules from larger ones) in a solution by interposing a semipermeable membrane between the solution and water. The crystalloid substances or smaller molecules pass through the membrane into the water on the other side. The colloids do not. Hemodialysis is the dialysis of soluble substances and water from the blood by diffusion through semipermeable membrane. Separation of cellular elements and colloids from soluble substances is achieved by differential pore size in the membrane and rates of diffusion.

A hemodialysis unit is connected to a patient's body by means of a catheter. The catheter is inserted partially within the body with its distal end placed in a blood vessel and its proximal end connected to the hemodialysis unit. The catheter can be a rigid metal device such as a needle or a flexible plastic device such as a cannula. A double lumen catheter has two lumens that allow both irrigation and aspiration. For example, a double lumen catheter can be used for removing blood from a fistula or vein for processing in the hemodialysis machine and for returning the processed blood back to the fistula or vein.

During hemodialysis, a patient's blood flows through the catheter to an extracorporeal circuit consisting of blood lines and the hemodialysis unit. The unit provides and controls the flow of blood. Inside the unit, blood passes the inner lumens of thousands of capillary membranes. Uremic toxins accumulated in the patient's blood diffuse through the membrane while blood cells and proteins are retained. Outside the membranes, a constant flow of dialysate (an aqueous solution containing physiologic salts) removes the uremic toxins. At the same time, water is extracted from the patient's blood by ultrafiltration and purified blood is channeled back into a body by means of the catheter.

A hemodialysis patient's blood must be adequately and completely treated. A number of medically adverse effects result from incomplete elimination of toxins. Performance of a hemodialysis unit is affected by factors related to the patient's vascular access such as degree of access recirculation, cardiopulmonary recirculation, access flow and suction pressure developed by the hemodialysis blood pump as it pulls blood into the extracorporeal hemodialysis circuit. See Keshaviah, U.S. Pat. No. 5,507,723. Parameters that may be varied to achieve adequate hemodialysis include blood flow rate, dialysis solution flow rate, dialyzer competency and temperature. Generally, raising blood flow rate increases dialyzer clearance of small molecular weight solutes. Consequently, higher blood flow rates have been used to improve dialysis clearance efficiency. However, conditions such as access recirculation decrease clearance. Access recirculation is the recirculation of treated blood back into the hemodialyzer system. Access recirculation reduces clearance of solutes and causes inadequate dialysis. Recirculation reduces the effective blood flow and diminishes the efficiency of the hemodialysis process. Generally blood recirculation values of more than 15 percent are unacceptable.

Changes in catheter design have been suggested for the purpose of reducing access recirculation. Apertures of intake and outflow lumens have been longitudinally spaced 20–30 mm apart to prevent recirculation. For example, Twardowski et al. U.S. Pat. No. 5,569,182 discloses that the lumen for outflow of blood back into the vein should terminate beyond the lumen for inflow. The purpose of this is to prevent cleansed blood from reentering the blood outlet needle and returning to the dialysis machine. However, longitudinal spacing of the apertures in of itself, does not adequately diminish access recirculation.

There remains a need for a double lumen catheter that addresses problems of access recirculation and inadequate flow rates.

SUMMARY OF THE INVENTION

The invention relates to a double lumen catheter that accommodates increased flow rates and minimizes access recirculation. The catheter comprises an elongated tube that has unitary outer walls. A longitudinal planar septum divides the interior of the tube into an inlet lumen and a longer return lumen. The inlet lumen extends from a proximal end of the tube to an end terminating in a distally forward facing aperture. The return lumen extends contiguously with the inlet lumen from the proximal end of the tube to an end terminating in a distally forward facing aperture spaced in the longitudinal direction distally forward of the inlet lumen aperture. A diverting structure extends from an outer wall of the return lumen distally forward of the aperture of the inlet lumen. The diverting structure diverts flow of treated fluid discharged from the return lumen away from the distally forward facing aperture of the inlet lumen.

The invention also relates to a blood purification system, comprising a dialysis unit for purifying a patient's blood and a dual lumen catheter with diverting structure coupled to a dialysis unit.

In a final aspect, a method is provided for circulating blood through the double lumen catheter wherein blood is withdrawn from a vein through the inlet aperture of the inlet lumen and after treatment is discharged by means of the catheter back into the vein through the aperture of the return lumen. Blood discharged from the catheter is diverted away from the aperture of the inlet lumen.

BRIEF DESCRIPTION OF THE DRAWINGS

FIG. 1 is a perspective view of a double lumen catheter according to the invention;

FIG. 2 is a side view of a double lumen catheter with substantially straight barrel;

FIG. 3 is a side view of a double lumen catheter with tapered barrel;

FIG. 4 is a cross section side view of the catheter of FIG. 2;

FIG. 5 is a sectional view along lines A—A of FIG. 2;

FIG. 6 is a sectional view along lines B—B of FIG. 2;

FIG. 7 shows a blood purification system including the double lumen catheter of FIGS. 1, 2 and 4 to 6;

FIG. 8 is a schematic representation of a front portion of a catheter with sloped apertures but without a diverting structure;

FIG. 9 is the same catheter as FIG. 8 but with a diverting structure.

FIG. 10 is the same catheter as FIG. 9 but with increased distance between apertures;

FIG. 11 is the same catheter as FIG. 10, but with an increased flow area and with a diverting structure with slanted distal face; and FIG. 12 is the same catheter as FIG. 11, but with decreased outer diameter.

DETAILED DESCRIPTION OF THE INVENTION

Mahurkar U.S. Pat. No. 4,134,402 discloses a double lumen continuous flow hemodialysis needle or cannula having contiguous lumens of different lengths. The shorter lumen acts as a blood intake lumen and the longer lumen as a blood return lumen. The end of the return lumen extends beyond the end of the intake lumen. The distance by which the return lumen extends beyond the intake lumen is determined by the rate of blood flow in the vein or fistula, the angle of entrance of the double lumen needle and the size of the vein or fistula. The needle or cannula has an internal planar axial divider between the lumens that forms a common inner wall of each lumen. Each lumen has a beveled edge sloping outwardly and away from the needle formed by the common wall between lumens. Each of the lumens defines a blood flow path parallel to the other such that blood entering the intake lumen and blood leaving the return lumen flow in a direction substantially parallel to the vessel wall. Mahurkar '402 discloses a distance "d" between the intake aperture and return aperture of ½ inch to ¾ inch. (12.7 mm to 19.1 mm). Edges of the apertures are sloped outwardly and away from the needle formed at the longitudinal axis of the catheter. The apertures are sloped to promote insertion of the needle.

In another embodiment, the Mahurkar '402 catheter is a double lumen catheter with a first blood intake lumen with a blood intake port on its barrel and a second blood intake lumen rotatably and removably interposed in the first lumen and also having a blood intake port on its barrel. The inner intake lumen can be rotated to align its port with the port of the outer lumen to permit intake of blood into the inner intake lumen.

Mahurkar U.S. Pat. No. 4,808,155 discloses a double lumen catheter with a tube that terminates with a blunt distal end normal to the axis of the catheter. The catheter does not have a conical tip or taper as does the Mahurkar '402 catheter. Mahurkar '155 states that the absence of the conical tip avoids trauma and migration of the catheter into the tributaries of the veins. The blunt end prevents the end of the catheter from traumatizing or becoming caught in the walls of a blood vessel.

Mahurkar U.S. Pat. No. 5,197,951 discloses a double lumen catheter with a tube that terminates with a blunt distal end. The distal ends of both lumens terminate at the blunt distal end of the tube. The intake lumen has a side wall aperture separated from the aperture of the return lumen and a solid terminal portion distal to its aperture to prevent voids in the blood flow path.

Mahurkar, U.S. Pat. No. 4,583,968 discloses return and inlet apertures that are circumferentially disposed along the longitudinal axis of a cylindrical catheter tube. Viewed from the side, the apertures are seen to have scaphoid (boat shaped) margins. These apertures are kept at a small size in order to reduce insertion trauma. However, the small size impedes fluid flow.

The present invention provides a double lumen catheter that effectively reduces access recirculation and fluid pressure in the vicinity of an inlet aperture. The catheter is characterized by a diverting structure located distally of the intake aperture. In one embodiment, the diverting structure is in the form of a truncated frustum that completes a phantom outline of a projected extension or taper of the catheter barrel. The diverting structure functions as a foil or diverter to reduce access recirculation of treated blood discharged from the outlet aperture. At the same time, the flow diverter is placed sufficiently distal to the inlet aperture to permit rapid and even flow into the inlet lumen. Additionally, the catheter can be characterized by an intake aperture that is a beveled cut open end of the intake lumen. This feature increases pressure in the vicinity of the catheter and makes possible the high flow rates required for effective hemodialysis.

These and other features will become apparent from the following detailed discussion with reference to the drawings, which by way of example without limitation describes preferred embodiments of the present invention. In all the figures of the drawings, like structures are identified by the same numbers.

FIGS. 1 to 2 and 4 to 6 show various views of a smooth bore double lumen catheter 10 according to the invention. The catheter 10 has an elongated hollow tube 12, which is inserted into a cavity of the body such as a fistula or vein. Tube 12 is shown with proximal end 14 and distal end 16. Tube 12 of catheter 10 is circular in cross section as shown in FIG. 5 and FIG. 6. The tube 12 has an internal divider or septum 18. The tube 12 and septum 18 define inlet lumen 20 and return lumen 22. The lumens 20 and 22 are semicircular or "D" shaped.

Septum 18 extends along the longitudinal axis of tube 12 from a branching connector 24 at proximal end 14. Branching connector 24 connects the distal end portions of inlet lumen 20 and return lumen 22 to respective fluid inlet line 26 and fluid return line 28. Fluid inlet line 26 and fluid return line 28 can be respective arterial line and venous line of a treatment device or circuit such as a dialysis circuit.

Inlet lumen 20 includes inlet aperture 30 at its distal end to admit flow of fluid between the body cavity and the lumen 20. The return lumen 22 is longer than inlet lumen 20. Return lumen 22 extends along the entire length of tube 12 and includes return aperture 32 at its distal end to return fluid to the body.

Inlet lumen aperture 30 is defined by an outer inlet aperture wall lip 34 that tapers away from septum 18 in a proximal direction. Similarly, return lumen aperture 32 is defined by an outer return aperture wall lip 36 that tapers away from septum 18 in a proximal direction. The tapers of the inlet lumen aperture 30 and return lumen aperture 32 are designed to reduce access recirculation by biasing inlet and return flow patterns away from the direction of blood recirculation.

The extension of return lumen 22 in the proximal direction beyond the inlet lumen 20 defines a flat return lumen outer surface 38 as an extension of a surface of septum 18. Diverting structure 40 is located proximal to inlet aperture 30 as a continuation of the outer curved surface of return lumen 22. During operation of a catheter, pressure is reduced in the vicinity of an inlet aperture. The lower pressure can cause collapse of blood vessels and narrowing of the host fistula or vein. According to the present invention, diverting structure 40 functions as a flow divider or diverter to reduce access recirculation and to raise fluid pressure in the vicinity of inlet aperture 30. The diverting structure 40 can be any shape or form so long as the diverting structure functions to divert recirculation flow from return aperture 32 away from inlet aperture 30. As shown, the diverting structure 40 is shoulder-shaped and completes a phantom outline of inlet lumen 20 projected in a proximal direction from the inlet lumen aperture 30. In other embodiments, the diverting structure forms a wall in front of the inlet lumen 20 or has a semicircular profile or a fluid dynamic scoop profile from distal face to proximal face. The diverting structure 40 can be any shape so long as it diverts or deflects flow from a distal direction away from the inlet lumen 20. The diverting structure of FIG. 9 has a straight face 52 opposed to flow from a distal direction including recirculation flow from outlet aperture 32. The diverting structure of FIGS. 1 to 7 has a slanted face 54 opposed to recirculation flow. A slanted face shape is particularly advantageous because it smoothly merges with the body of the tube 12 to minimize tube insertion trauma.

The distance d, between inlet aperture 30 and return aperture 32 can be about 20 mm to about 45 mm, desirably about 25 mm to about 40 mm and preferably about 30 mm to about 35 mm. Outer wall thickness of tube 12 can be about 0.06 mm to about 0.35 mm, desirably about 0.11 mm to about 0.30 mm and preferably about 0.16 mm to about 0.25 mm. The thickness of septum 18 can be about 0.07 mm to about 0.38 mm, desirably about 0.12 mm to about 0.33 mm and preferably about 0.17 mm to about 0.28 mm. Since the size of catheter 10 may vary with the particular host body, meaningful dimensions are defined in terms of their ratio to outside diameter of the catheter at its widest point. The ratio of distance d to catheter outside diameter can be about 5 to about 12, desirably about 6 to about 10 and preferably about 7 to about 9. The ratio of outer wall thickness to outside diameter can be about 0.01 to about 0.09, desirably about 0.02 to about 0.08 and preferably about 0.04 to about 0.07. The ratio of septum thickness to outside diameter can be about 0.01 to about 0.1, desirably about 0.03 to about 0.09 and preferably about 0.04 to about 0.07.

FIG. 3 illustrates another embodiment of the invention. In FIG. 3, like numbers to the numbers of FIGS. 1, 2 and 4 to 6 illustrate like structures. In FIG. 3, distal end 16 of tube 12 has a truncated conical tip designated 42. The truncated conical tip 42 smoothly merges with the cylindrical body of the tube 12. The outer circumference of the catheter 10 converges in a gradual taper at distal end 16 to define the truncated conical tip 42. The truncated conical tip 42 is centered on the axis of the cylindrical body of the tube 12 to serve as a guidance point for insertion of catheter 10 and to uniformly distribute frictional resistance encountered by the truncated conical tip 42 when catheter 10 is inserted into a body cavity.

FIG. 7 of the drawings shows a blood purification system including the double lumen catheter of FIGS. 1, 2 and 4 to 6. In FIG. 7, blood purification system 44 includes a dialysis unit 46 for purifying a patient's blood and a double lumen catheter 10 coupled to the dialysis unit 46 by inlet line 48, which connects to inlet lumen 20, and return line 50, which connects to return lumen 22.

In operation, blood is circulated through the double lumen catheter of FIGS. 1, 2 and 4 to 7 by first withdrawing blood from a vein through aperture 30 of the inlet lumen 20. The blood travels to the dialysis unit 46 via line 48. The blood is treated in the dialysis unit and returned to catheter 10 via line 50. The treated blood is discharged from catheter 10 into the vein through aperture 32 of return lumen 22. According to the invention, blood discharged from catheter 10 via return aperture 32 that tends to flow back toward inlet aperture 30 is diverted away from the aperture 30 by diverting structure 40 located in front of aperture 30 of the inlet lumen 20.

The improvement of the double lumen catheter of the invention is demonstrated in the following example.

EXAMPLE

"Computational Fluid Dynamics" was used as a mathematical modeling technique to analyze catheter flow characteristics. This modeling technique is based on laws of conservation of mass and momentum of fluid in three-dimensional space and in time. Mathematical equations of the technique from a system of complex non-linear partial differential equations known as the Navier-Stokes equations. Simplifying assumptions were made to solve the equations to provide a system of mathematical equations that defined a geometric 3-D model for a catheter inserted centrally into a host vessel along a flow axis. The model simulated flow of undialyzed blood and dialyzed blood in the region of interest. A flow domain consisted of flow portions of the host vessel upstream and downstream of the catheter tip as well as flow portions of the inflow and outflow lumen. The flow domain was divided by a mesh into discrete computational cells. A governing system of the mathematical equations was then solved for prescribed values of host vessel flow rate and catheter flow rate. Various catheter configurations were simulated and evaluated by the technique.

A first computationally configured catheter was developed representing a conventional catheter. A second catheter represented the conventional catheter but with 45° sloped apertures. The front end of the second catheter is illustrated schematically in FIG. 8. A third computational catheter was developed representing the catheter of FIG. 8 but modified with a flow diverting structure 40. The diverting structure 40 had a straight-up distal face and a 60° sloped proximal face with a 2 mm by 10 mm base. The front end of this catheter is shown in FIG. 9. FIG. 10 is the same catheter as FIG. 9 but with increased distance between apertures. The distance was 32 mm. FIG. 11 is the same catheter as FIG. 10, but with an increased flow area and with a diverting structure with slanted distal face. The face was slanted 45°. FIG. 12 is the same catheter as FIG. 11, but with decreased outer diameter.

Performance was evaluated for all catheters at a catheter flow rate of 250 ml/min, a typical flow rate during clinical use. Vein flow was chosen equal to catheter flow to ensure a high degree of sensitivity of access recirculation to catheter design differences. The catheter of FIG. 8 showed a 30% decrease in access recirculation rate, 20% decrease in strain rate and 10% increase in fluid pressure in the vicinity of the inlet aperture compared to the conventional catheter without sloped apertures. The catheter of FIG. 9 showed a 46% decrease in access recirculation rate, a 21% decrease in strain and a 9% increase in aperture vicinity pressure contrasted to the conventional catheter. The catheter of FIG. 10 showed an 81% decrease in access recirculation rate, a 21% decrease in strain and a 6% increase in aperture vicinity pressure contrasted to the conventional catheter. The catheter of FIG. 11 showed an 87% decrease in access recirculation rate, a 35% decrease in strain and a 21 increase in aperture vicinity pressure contrasted to the conventional catheter. The catheter of FIG. 12 showed a 77% decrease in access recirculation rate, a 48% decrease in strain and a 58% increase in aperture vicinity pressure contrasted to the conventional catheter.

While preferred embodiments of the invention have been described, the present invention is capable of variation and modification and therefore should not be limited to the precise details of the examples. The invention includes changes and alterations that fall within the purview of the following claims.

What is claimed:

1. A double lumen catheter comprising an elongated tube having unitary outer walls and a longitudinal planar septum dividing an interior of said tube into an inlet lumen defined by an outer wall and said septum and a longer return lumen, said inlet lumen extending from a proximal end of said tube to an end terminating in a distally forward facing aperture that terminates said outer wall of said inlet lumen to form a wall-less open spacing defined solely by said septum, said return lumen extending substantially contiguously with said inlet lumen from said proximal end of said tube to an end terminating in a distally forward facing aperture spaced in the longitudinal direction distally forward of said inlet lumen aperture, wherein said inlet lumen aperture is defined by an outer wall lip that tapers away from said septum in a proximal direction and said return is defined by an outer wall lip that tapers away from said septum in a proximal direction and a diverting structure extending from said outer wall of said return lumen and positioned distally forward of said aperture of said inlet lumen and said spacing and noncontiguous to said aperture to divert flow of treated fluid discharged from said return lumen away from said distally forward facing aperture of said inlet lumen.

2. The double lumen catheter of claim 1, having uniform outside diameter.

3. The double lumen catheter of claim 2, wherein a ratio of distance between said inlet lumen aperture and said return lumen aperture to said outside diameter of said catheter is about 5 to about 12.

4. The double lumen catheter of claim 2, wherein a ratio of distance between said inlet lumen aperture and said return lumen aperture to said outside diameter of said catheter is about 6 to about 10.

5. The double lumen catheter of claim 2, wherein a ratio of distance between said inlet lumen aperture and said return lumen aperture to said outside diameter of said catheter is about 7 to about 9.

6. The double lumen catheter of claim 2, wherein a ratio of an outer wall thickness of said catheter to said outside diameter is about 0.01 to about 0.09.

7. The double lumen catheter of claim 2, wherein a ratio of an outer wall thickness of said catheter to said outside diameter is about 0.02 to about 0.08.

8. The double lumen catheter of claim 2, wherein a ratio of an outer wall thickness of said catheter to said outside diameter is about 0.04 to about 0.07.

9. The double lumen catheter of claim 2, wherein a ratio of thickness of said septum to said outside diameter is about 0.01 to about 0.10.

10. The double lumen catheter of claim 2, wherein a ratio of thickness of said septum to said outside diameter is about 0.03 to about 0.09.

11. The double lumen catheter of claim 2, wherein a ratio of thickness of said septum to said outside diameter is about 0.04 to about 0.07.

12. A blood purification system, comprising:
a dialysis unit for purifying a patient's blood, and
the dual lumen catheter of claim 1 coupled to said dialysis unit.

13. A method of obtaining improved whole body dialysis clearance in a system according to claim 12, comprising;
withdrawing blood from a vein through an inlet aperture of an inlet lumen of a dual lumen catheter;
discharging blood from said catheter into said vein through a return aperture of a return lumen of said dual lumen catheter; and
diverting blood discharged from said catheter away from said inlet aperture of said inlet lumen to increase fluid pressure in the vicinity of the of the inlet aperture.

14. The double lumen catheter of claim 1, wherein said diverting structure functions to reduce access recirculation and to raise pressure in the vicinity of said inlet aperture.

15. The double lumen catheter of claim 1, wherein said diverting structure is in the form of an extended phantom outline of said inlet lumen projected in said longitudinal direction distally forward of said inlet aperture.

16. The double lumen catheter of claim 1, wherein said elongated tube tapers to a tip at said inlet lumen aperture for insertion into a patient's body.

17. The double lumen catheter of claim 1 wherein said proximal end of said elongated tube diverges into branches, each branch containing a continuation of one of said lumens for connection to a hemodialysis apparatus.

18. The double lumen catheter of claim 1, wherein said distally forward facing inlet aperture is the sole aperture to admit fluid into said inlet lumen and said distally forward facing return aperture is the sole aperture to discharge fluid from said return lumen.

19. The double lumen catheter of claim 1, wherein said diverting structure has a distally forward straight face extending from said outer wall of said return lumen.

20. The double lumen catheter of claim 1, wherein said diverting structure has a distally forward slanted face extending from said outer wall of said return lumen.

21. The double lumen catheter of claim 1, wherein said diverting structure comprises a slanted face opposed to said flow of treated fluid.

22. The double lumen catheter of claim 1, wherein said diverting structure comprises a shoulder shape.

23. The double lumen catheter of claim 1, wherein said diverting structure comprises a wall.

24. The double lumen catheter of claim 1, wherein said diverting structure comprises a semicircular profile.

25. The double lumen catheter of claim 1, wherein said diverting structure comprises a fluid dynamic scoop profile from distal face to proximal face.

* * * * *